(12) United States Patent
Crocker et al.

(10) Patent No.: US 6,699,170 B1
(45) Date of Patent: *Mar. 2, 2004

(54) RADIATION DELIVERY BALLOON CATHETER

(75) Inventors: Michael Crocker, Anaheim, CA (US); George F. Kick, Laguna Niguel, CA (US); Mark A. Siminuk, Lake Forest, CA (US)

(73) Assignee: Endologix, Inc., Irvine, CA (US)

( * ) Notice: Subject to any disclaimer, the term of this patent is extended or adjusted under 35 U.S.C. 154(b) by 48 days.

This patent is subject to a terminal disclaimer.

(21) Appl. No.: 09/688,396

(22) Filed: Oct. 16, 2000

Related U.S. Application Data

(63) Continuation of application No. 09/543,710, filed on Apr. 5, 2000, now abandoned, which is a continuation of application No. 09/119,828, filed on Jul. 21, 1998, now Pat. No. 6,176,821, which is a continuation of application No. 08/789,969, filed on Jan. 31, 1997, now Pat. No. 5,782,742.

(51) Int. Cl.⁷ .................................................. A61N 5/00
(52) U.S. Cl. ........................................................ 600/3
(58) Field of Search .......................................... 600/1–9

(56) References Cited

U.S. PATENT DOCUMENTS

| | | |
|---|---|---|
| 3,324,847 A | 6/1967 | Zoumboulis |
| 4,115,536 A | 9/1978 | Rothman et al. |
| 4,124,705 A | 11/1978 | Rothman et al. |
| 4,126,669 A | 11/1978 | Rothman et al. |
| 4,225,790 A | 9/1980 | Parsons, Jr. et al. |
| 4,423,725 A | 1/1984 | Baran et al. |
| 4,581,017 A | 4/1986 | Sahota |
| 4,588,395 A | 5/1986 | Lemelson |
| 4,655,771 A | 4/1987 | Wallsten |
| 4,674,480 A | 6/1987 | Lemelson |
| 4,706,652 A | 11/1987 | Horowitz |
| 4,762,129 A | 8/1988 | Bonzel |
| 4,815,449 A | 3/1989 | Horowitz |
| 4,819,618 A | 4/1989 | Liprie |
| 4,878,492 A | 11/1989 | Sinofsky et al. |
| 4,946,435 A | 8/1990 | Suthanthiran et al. |
| 4,994,013 A | 2/1991 | Suthanthiran et al. |
| 5,011,677 A | 4/1991 | Day et al. |
| 5,019,369 A | 5/1991 | Presant et al. |
| 5,040,548 A | 8/1991 | Yock |

(List continued on next page.)

FOREIGN PATENT DOCUMENTS

| | | |
|---|---|---|
| DE | 392700 A1 | 2/1991 |
| EP | 0 433 011 B1 | 7/1994 |
| EP | 0 688 580 A1 | 12/1995 |

(List continued on next page.)

OTHER PUBLICATIONS

Radiation Quantities and Units. ICRU Report 33, International Commission on Radiation. Units and Measurements Apr. 15, 1980.

(List continued on next page.)

*Primary Examiner*—Samuel G. Gilbert
(74) *Attorney, Agent, or Firm*—Knobbe, Martens, Olson & Bear, LLP

(57) ABSTRACT

Disclosed is a balloon catheter having an inflatable balloon having a radiation carrier such as a radiation delivery layer thereon. In one embodiment, the radiation delivery layer comprises one or more layers of metal foil, such as gold. The foil is irradiated, and the balloon is thereafter positioned at a treatment site in a vessel and expanded to bring the metal foil layer into close proximity with the vessel wall. In another embodiment, the radiation carrier is in the form of a dopant in the balloon material. Methods of using the balloon include radiation dosing a site following a balloon dilatation or other procedure, and simultaneously performing balloon angioplasty and radiation dosing.

64 Claims, 5 Drawing Sheets

U.S. PATENT DOCUMENTS

| | | | |
|---|---|---|---|
| 5,059,166 A | 10/1991 | Fischell et al. |
| 5,061,273 A | 10/1991 | Yock |
| 5,106,360 A | 4/1992 | Ishkiwara et al. |
| 5,152,747 A | 10/1992 | Oliver |
| 5,163,896 A | 11/1992 | Suthanthiran et al. |
| 5,176,617 A | 1/1993 | Fischell et al. |
| 5,199,939 A | 4/1993 | Dake et al. |
| 5,213,561 A | 5/1993 | Weinstein et al. |
| 5,267,960 A | 12/1993 | Hayman et al. |
| 5,302,168 A | 4/1994 | Hess |
| 5,302,369 A | 4/1994 | Day et al. |
| 5,342,283 A | 8/1994 | Good |
| 5,354,257 A | 10/1994 | Roubin et al. |
| 5,411,466 A | 5/1995 | Hess |
| 5,424,288 A | 6/1995 | Order |
| 5,484,384 A | 1/1996 | Fearnot |
| 5,498,227 A | 3/1996 | Mawad |
| 5,503,613 A | 4/1996 | Weinberger |
| 5,540,659 A | 7/1996 | Teirstein |
| 5,605,530 A | 2/1997 | Fischell et al. |
| 5,616,114 A | 4/1997 | Thornton et al. |
| 5,618,266 A | 4/1997 | Liprie |
| 5,643,171 A | 7/1997 | Bradshaw et al. |
| 5,653,683 A | 8/1997 | D'Andrea |
| 5,662,580 A | 9/1997 | Bradshaw et al. |
| 5,674,177 A | 10/1997 | Hehrlein et al. |
| 5,683,345 A | 11/1997 | Waksman et al. |
| 5,688,220 A | 11/1997 | Verin et al. |
| 5,707,332 A | 1/1998 | Weinberger |
| 5,713,828 A | 2/1998 | Coniglione |
| 5,720,717 A | 2/1998 | D'Andrea |
| 5,722,984 A | 3/1998 | Fischell et al. |
| 5,728,042 A | 3/1998 | Schwager |
| 5,730,698 A | 3/1998 | Fischell |
| 5,755,690 A | 5/1998 | Saab |
| 5,762,631 A | 6/1998 | Klein |
| 5,762,903 A | 6/1998 | Park et al. |
| 5,782,740 A | 7/1998 | Schneiderman |
| 5,782,741 A | 7/1998 | Bradshaw et al. |
| 5,782,742 A | 7/1998 | Crocker et al. |
| 5,795,286 A | 8/1998 | Fischell et al. |
| 5,840,008 A | 11/1998 | Klein et al. |
| 5,840,009 A | 11/1998 | Fischell et al. |
| 5,860,991 A | 1/1999 | Klein et al. |
| 5,863,284 A | 1/1999 | Klein |
| 5,871,436 A | 2/1999 | Evry |
| 5,879,282 A | 3/1999 | Fischell et al. |
| 5,911,717 A | 6/1999 | Jacobson et al. |
| 5,919,126 A | 7/1999 | Armini |
| 5,980,566 A | 11/1999 | Alt et al. |
| 6,013,019 A | 1/2000 | Fischell et al. |
| 6,019,718 A | 2/2000 | Hektner |
| 6,024,690 A | 2/2000 | Lee et al. |
| 6,033,357 A | 3/2000 | Ciezki et al. |
| 6,042,600 A | 3/2000 | Rosenthal et al. |
| 6,045,495 A | 4/2000 | Weinberger |
| 6,050,930 A | 4/2000 | Teirstein |
| 6,059,713 A | 5/2000 | Urick et al. |
| 6,059,714 A | 5/2000 | Armini et al. |
| 6,059,752 A | 5/2000 | Segal |
| 6,071,227 A | 6/2000 | Popowski et al. |
| 6,077,413 A | 6/2000 | Hafeli et al. |
| 6,103,295 A | 8/2000 | Chan et al. |
| 6,176,821 B1 * | 1/2001 | Crocker et al. ............... 600/3 |

FOREIGN PATENT DOCUMENTS

| | | |
|---|---|---|
| EP | 0593 136 B1 | 3/1997 |
| WO | WO 93/04735 | 3/1993 |
| WO | WO 94/23789 | 10/1994 |
| WO | WO 94/26205 | 11/1994 |
| WO | WO 95/19807 | 7/1995 |
| WO | WO 95/29008 | 11/1995 |
| WO | WO 96/10436 | 4/1996 |
| WO | WO 96/13303 | 5/1996 |
| WO | WO 96/14898 | 5/1996 |
| WO | WO 96/22121 | 7/1996 |
| WO | WO 97/18012 | 5/1997 |

OTHER PUBLICATIONS

Effects of high–dose intracoronary irradiation on vasomotor function and smooth muscle histopathology. Joseph G. Wiedermann, Jeffrey A. Leavy, Howard Amols, Allan Schwartz, Shunichi Homma, Charle Marboe and Judah Weinberger. Interventional Cardiology Center, Department of Medicine and Radiation Oncology and Section of Cardiac Pathology. Columbia –Presbyterian Medical Center and Columbia University, 1994 the American Physiological Society.

Intracononary Irradiation Markedly Reduces Restenosis After Balloon Angioplasty in a Porcine Model. Joseph G. Wiedermann, M.D., Charles Marboe, M.D., Howard Amols, Ph.D., Allan Schwartz, M.D., FACC, Judah Weinberger, M.D., Ph.D., FACC, JACC vol. 23, No. 6, May 1994: 1491–8.

Intracoronary Irradiation Markedly Reduces Neointimal Proliferation After Balloon Angioplasty in a Swine: Persistent Benefit at 6–Month Follow–up. Jospeh G. Wiedermann, M.D., Charles Marboe, M.D., Howard Amols, Ph.D., Allan Schwartz, M.D., FACC, Judah Weinberger, M.D., Ph.D., FACC, JACC, vol. 25, No. 6, May 1995: 1451–6.

Discoveries in Radiation for Restenosis. Emory University of School of Medicine. Presented by the Andreas Gruentzig Cardiovascular Center and the Department of Radiation Oncology of Emory University School of Medicine: J.W. Marriott Hotel at Lenox. Atlanta, GA, Jan. 11–12. 1996.

Cell–Survival Curves. Radiobiology for the Radiologist. Eric J. Hall, D. Phil., D. Sc., F.A.C.R., Third Edition, J.B. Lippincott Company, Philadelphia.

Abstracts From the 66th Scientific Sessions Georgia World Congress Center, Supplement to Circulation, American Heart Association, Atlanta, Georgia, Nov. 8–11. 1993.

The Dose Distribution Produced by a 32p–Coated Stent, W. V. Prestwich and T.J. Kennet. Medical Physics, vol. 22 No. 3, Mar. 1995.

Abstracts From the 67th Scientific Sessions Dallas Convention Center, Circulation, American Heart Association Dallas, Texas, Nov. 14–17, 1994.

Pure B–Particle–Emitting Stents Inhibit Neointima Formation in Rabbits. Christoph Hehrlein, M.D.: Marc Stintz, B.S.: Ralf Kinscherf, Ph.D.,: Klaus Schlosser, Ph.D., Enrhard Huttel, Ph.D.: Peter Fehsenfeld, Ph.D,: Wolfgang Kubler, M.D.: American Heart Assoication, Circulation, vol. 93, No. 4, Feb. 15, 1996.

Radioactive Balloon Catheter to Inhibit Restenosis after Angioplasty.

Prophylactic Endovascular Radiotherapy to Prevent Intimal Hyperplasia After Stent Implanation in Femorpopliteal Arteries, Dieter Lierman, Heinz, D., Bottcher, Jurgen Kollath, Bernd Schopohl, Gerd Strassmann Ernst–P. Strecker, Karl H. Breddin: Cardiovascular and Interventional Radiology. (1994) 17:12–16.

* cited by examiner

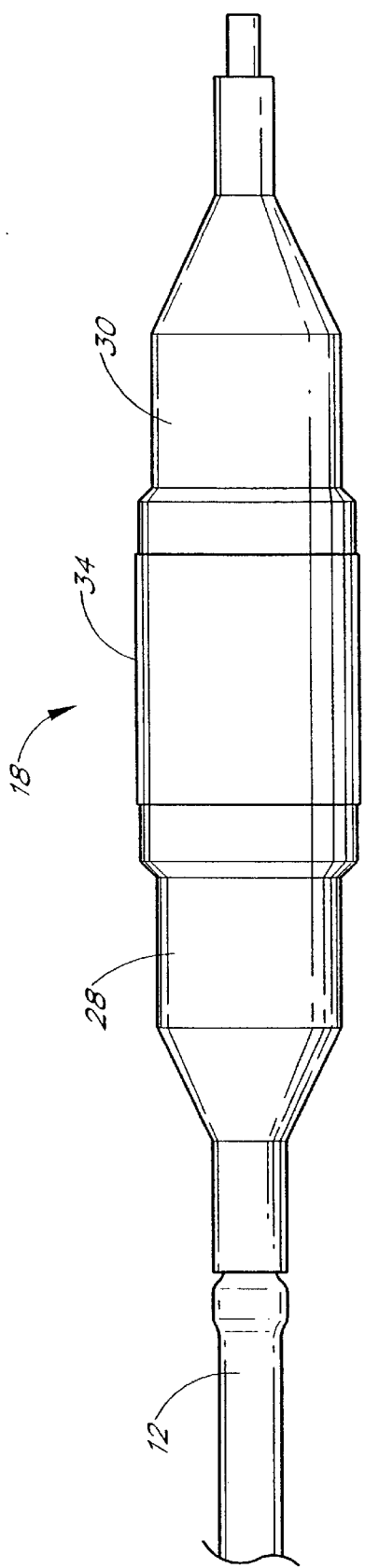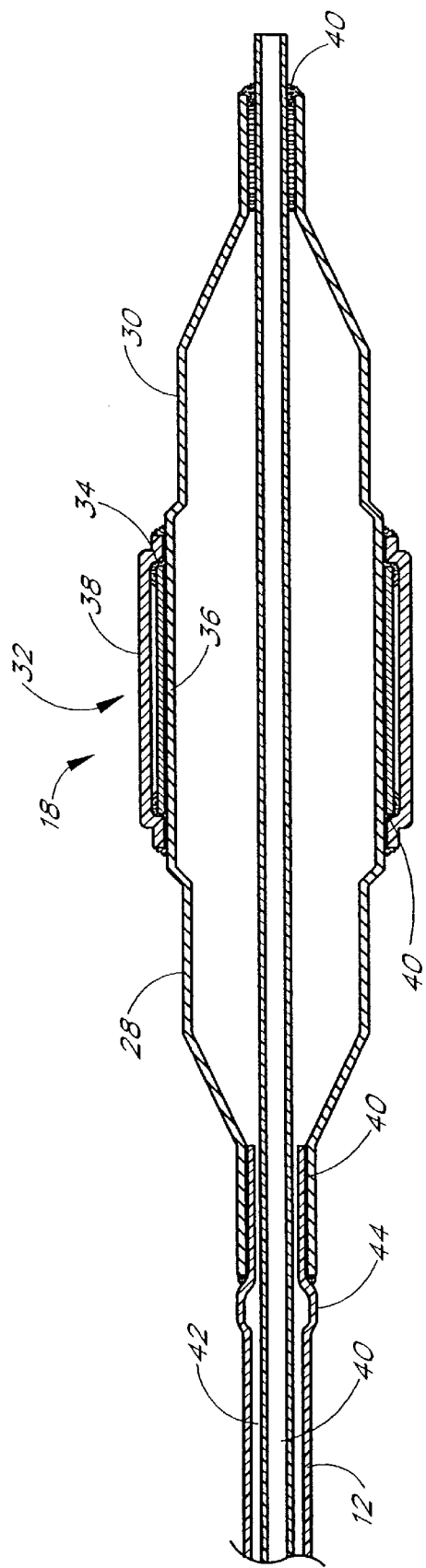

$$V_{\text{AFFECTED TISSUE}} = \tfrac{4}{3}\pi R^3$$

$$V_{\text{AFFECTED TISSUE}} = \ell\pi(R + D)^2 - \ell\pi R^2$$

RADIATION DELIVERY BALLOON CATHETER

This is a continuation application Ser. No. 09/543,710, filed Apr. 5, 2000, now abandoned, which is a continuation of U.S. application Ser. No. 09/119,828 filed on Jul. 21, 1998, now U.S. Pat. No. 6,176,821, which is a continuation application of U.S. application Ser. No. 08/789,969 filed on Jan. 31, 1997, now U.S. Pat. No. 5,782,742.

BACKGROUND OF THE INVENTION

The present invention relates to radiation delivery systems, and, in particular, to a radiation delivery balloon in which the radiation source is carried in the wall of the balloon.

Percutaneous transluminal coronary angioplasty ("PTCA") has become an established treatment for occlusive coronary artery disease. A catheter having an inflatable balloon secured to its distal end is advanced through an artery to a narrow region. The balloon is then inflated with a fluid from an external source, causing the narrowed region of the artery to be expanded. The balloon is then deflated and withdrawn. A variety of additional techniques have been developed for restoring patency to a narrowed vessel, including, for example, laser angioplasty and rotational arthrectomy. Although such techniques have enabled a minimally invasive treatment for patients who may otherwise would have been subjected to open heart surgery, long-term follow-up shows that a renarrowing of the vessel or restenosis frequently occurs.

Several studies document a restenosis rate of from about 25% to as much as 35% or more within the first year following PTCA, with the vast majority of patients requiring repeat procedures within six months. In addition, the restenosis rate for angioplasty of the smaller, peripheral arteries also occurs at a significant rate.

Immediate restenosis, also known as abrupt reclosure, results from flaps or segments of plaque and plaque-ridden tissue which are formed during balloon angioplasty and which can block the artery. Such blockage of the artery requires emergency surgery and often results in death. Furthermore, the possibility of an acute reclosure may require that a surgical team stand by during the balloon angioplasty procedure. Restenosis at a later time results from causes that are not fully understood. One mechanism believed responsible for restenosis is fibrointimal proliferation of the stretched wall in which the injured endothelial cells lining the vascular structure multiply and form obstructive fibrous tissue. Fibrointimal proliferation of the vascular wall involves cellular multiplication at a high rate, thereby causing an obstruction to flow through the vascular structure. Often repeat balloon angioplasty or surgery is required, and another episode of restenosis may occur.

At present, there is no effective method for preventing restenosis following angioplasty, arthrectomy, or any of the variety of additional lesser used techniques for restoring patency to a vascular stenosis. However, a variety of techniques have been explored for minimizing restenosis following angioplasty.

For example, a variety of catheters have been devised for delivering heat to the artery wall. See, for example, U.S. Pat. Nos. 4,878,492 and 4,646,737 to Hussein, et al., which are directed to the use of a laser as the heat source.

More recently, exposure of the dilated vascular site to a radioactive source has appeared to show more promise in inhibiting or delaying restenosis. As a consequence, a variety of radiation delivery vehicles have been designed.

For example, radioactive stents and radioactive guidewires are disclosed in U.S. Pat. No. 5,213,561 to Weinstein, et al. A variety of other radioactive catheter structures have also been devised, such as, for example, that disclosed in U.S. Pat. No. 5,199,939 to Dake, et al.

Notwithstanding the various efforts in the prior art to devise an effective radiation delivery system, the systems devised so far contain certain disadvantages. For example, delivery of a uniform dose of radiation circumferentially around the artery is difficult with the radioactive guidewire-type delivery systems, unless the guidewire is centered within the artery such as through the use of a balloon catheter. With the centered guidewire, the radiation dose must be sufficiently high to penetrate the centering catheter and blood or inflation media before penetrating the arterial wall. Radioactive stents may be able to provide a more circumferentially symmetrical delivery of radiation, but removal of an implanted stent is difficult or impossible as a practical matter. Thus, the clinician can exert relatively little control over the dosage delivered through such devices.

Thus, there remains a need for a radiation delivery vehicle for delivering a predetermined dosage of a low energy radiation to a site for a conveniently controllable period of time, for minimizing or delaying restenosis or other proliferative conditions.

SUMMARY OF THE INVENTION

There is provided in accordance with one aspect of the present invention a radiation delivery balloon catheter. The catheter comprises an elongate flexible tubular body, having a proximal end and a distal end. An inflatable balloon is provided on the tubular body near the distal end thereof, and the balloon is in fluid communication with an inflation lumen extending axially through the tubular body. A tubular metal foil layer is positioned on the balloon.

Preferably, an outer sleeve surrounds the tubular metal foil layer. In one embodiment, the metal comprises gold, having a thickness of no more than about 0.001 inches. The balloon catheter may be further provided with a perfusion conduit extending axially through the tubular body, in fluid communication with at least one proximal perfusion port on the tubular body on the proximal side of the balloon and at least one distal perfusion port on the tubular body on the distal side of the balloon.

In accordance with another aspect of the present invention, there is provided a multilayer radiation delivery balloon. The multilayer balloon comprises an inner inflatable layer having a radially inwardly directed surface and a radially outwardly directed surface. A radiation delivery layer is provided on the radially outwardly directed surface of the inner layer, and a tubular sleeve is disposed concentrically about the radiation delivery layer, for entrapping the radiation delivery layer against the radially outwardly directed surface of the balloon. In one embodiment, the radiation delivery layer comprises a metal layer, and the tubular sleeve comprises polyethylene terephthalate.

In accordance with a further aspect of the present invention, there is provided a method of treating a site within a vessel. The method comprises the steps of identifying a site in a vessel to be treated, and providing a radiation delivery catheter having an expandable balloon with a continuous annular radiation delivery layer thereon.

The balloon is positioned within the treatment site, and inflated to position the radiation delivery layer in close proximity to the vessel wall. A circumferentially substantially uniform dose of radiation is delivered from the delivery balloon to the vessel wall. The balloon is thereafter deflated and removed from the treatment site.

In accordance with a further aspect of the present invention, there is provided a method of simultaneously performing balloon dilatation of a stenosis in a body lumen and delivering radiation to the body lumen. The method comprises the steps of identifying a stenosis in a body lumen, and providing a treatment catheter having an elongate flexible tubular body with an inflatable balloon near the distal end and a cylindrical radiation delivery layer on the balloon.

The catheter is percutaneously inserted and transluminally advanced to position the balloon within the stenosis, and the balloon is inflated to radially expand the vessel in the area of the stenosis. Simultaneously, radiation is delivered from the metal layer to the vessel wall.

The catheter can be used to deliver radiation to any of a wide variety of sites in a body, such as arteries, veins, intestines, the colon, the trachea, the esophagus, the urethra, ureters, hollow organs, and other cavities, potential cavities and surgically created spaces. Nonmetal radiation carriers can also be used.

Further features and advantages of the present invention will become apparent to those of skill in the art in view of the detailed description of preferred embodiments which follows, when considered together with the attached claims.

BRIEF DESCRIPTION OF THE DRAWINGS

FIG. 3 is an enlarged side elevational view of a balloon of the type illustrated in FIG. 1.

FIG. 4 is a cross-sectional view of the balloon illustrated in FIG. 3.

DETAILED DESCRIPTION OF THE PREFERRED EMBODIMENT

Figure 1:
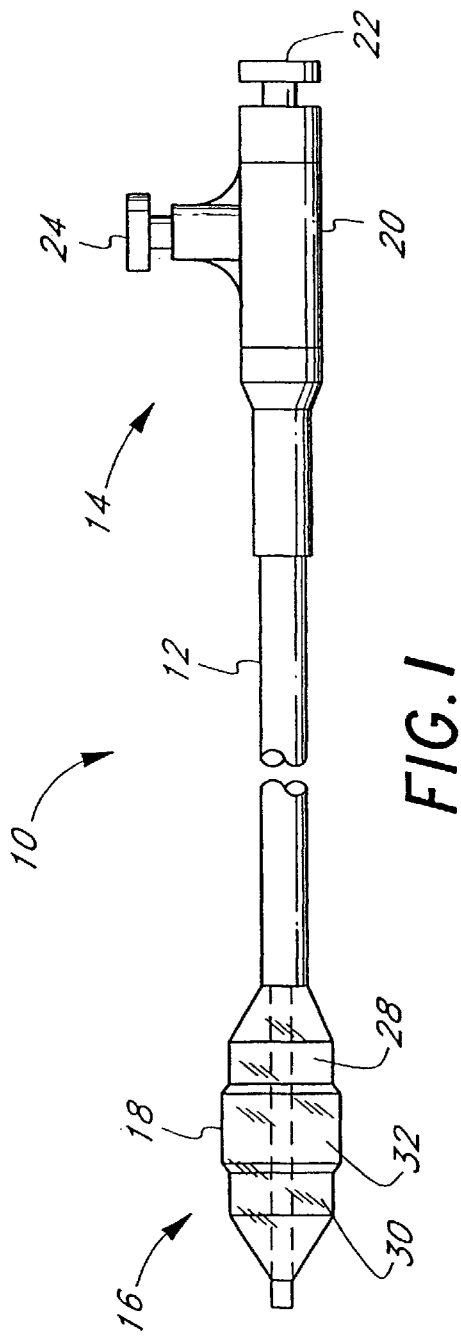
FIG. 1 is a schematic side elevational view of a first embodiment of a balloon catheter in accordance with the present invention.

Referring to FIG. 1, there is disclosed a radiation delivery catheter 10 in accordance with one aspect of the present invention. Although the description below is primarily directed to the radiation aspect of the invention, catheters embodying additional features known in the vascular dilatation art, such as carrying implantable stents, drug delivery, perfusion and dilatation features, or any combination of these features, can be used in combination with the balloon of the present invention as will be readily apparent to one of skill in the art in view of the disclosure herein.

The catheter 10 generally comprises an elongate tubular body 12 extending between a proximal control end 14 and a distal functional end 16. The length of the tubular body 12 depends upon the desired application. For example, lengths in the area of about 120 cm to about 140 cm are typical for use in radiation delivery following percutaneous transluminal coronary angioplasty.

The tubular body 12 may be produced in accordance with any of a variety of known techniques for manufacturing balloon-tipped catheter bodies, such as by extrusion of appropriate biocompatible plastic materials. Alternatively, at least a portion or all of the length of tubular body 12 may comprise a spring coil, solid walled hypodermic needle tubing, or braided reinforced wall, as is understood in the catheter and guide wire arts.

In general, tubular body 12, in accordance with the present invention, is provided with a generally circular cross-sectional configuration having an external diameter with the range of from about 0.02 inches to about 0.065 inches. In accordance with one preferred embodiment of the invention, the tubular body 12 has an external diameter of about 0.042 inches (3.2 f) throughout most of its length. Alternatively, generally triangular or oval cross-sectional configurations can also be used, as well as other noncircular configurations, depending upon the number of lumen extending through the catheter, the method of manufacture and the intended use.

In a catheter intended for peripheral vascular applications, the tubular body 12 will typically have an outside diameter within the range of from about 0.039 inches to about 0.065 inches. In coronary vascular applications, the tubular body 12 will typically have an outside diameter within the range of from about 0.026 inches to about 0.045 inches. Diameters outside of the preferred ranges may also be used, provided that the functional consequences of the diameter are acceptable for the intended purpose of the catheter. For example, the lower limit of the diameter for tubular body 12 in a given application will be a function of the number of fluid or other functional lumen, support structures and the like contained in the catheter, and the desired structural integrity.

In general, the dimensions of the catheter shaft and balloon can be optimized by persons of skill in the art in view of the present disclosure to suit any of a wide variety of applications. For example, the balloon of the present invention can be used to deliver radiation to large and small arteries and veins, as well as other lumens, potential spaces, hollow organs and surgically created pathways. The present inventors contemplate radiation delivery to the esophagus, trachea, urethra, ureters, fallopian tubes, intestines, colon, and any other location accessible by catheter which may benefit from radiation delivery. This includes surgically created lumens such as, for example, transjugular intrahepatic portosystemic shunts and others which will be recognized by those of skill in the art. Thus, although the present invention will be described below primarily in terms of coronary artery applications, it is understood that this is for illustrative purposes only, and the present invention has much broader applicability in the field of radiation delivery.

Tubular body 12 must have sufficient structural integrity (e.g., "pushability") to permit the catheter to be advanced to a treatment site such as distal arterial locations without buckling or undesirable bending of the tubular body 12. Larger diameters generally have sufficient internal flow properties and structural integrity, but reduce perfusion in the artery in which the catheter is placed. Larger diameter catheter bodies also tend to exhibit reduced flexibility, which can be disadvantageous in applications requiring placement of the distal end of the catheter in a remote vascular location. In addition, lesions requiring treatment are sometimes located in particularly small diameter arteries, necessitating the lowest possible profile.

As illustrated schematically in FIG. 1, the distal end 16 of catheter 10 is provided with at least one inflatable balloon 18. The proximal end 14 of catheter 10 is provided with a manifold 20 which may have one or more access ports, as is known in the art. Generally, manifold 20 is provided with a guide wire port 22 in an over the wire embodiment and a balloon inflation port 24. Additional access ports are provided as needed, depending upon the functional capabilities of the catheter 10. The balloon 18 can also be mounted on a rapid exchange type catheter, in which the proximal guidewire port 22 would not appear on the manifold 20 as is understood in the art. In a rapid exchange embodiment, the proximal guidewire access port is positioned along the length of the tubular body 12, such as between about 4 and 20 cm from the distal end of the catheter.

Referring to the embodiment of the balloon illustrated in FIG. 1 a focal or enlarged zone 32 is positioned between a proximal reference zone 28 and a distal reference zone 30. The relative lengths of each of the three zones may vary considerably depending upon the intended use of the balloon. In general, suitable dimensions of the balloon, both in terms of diameters and lengths, as well as other catheter dimensions, are disclosed in copending patent application Ser. No. 08/742,437, entitled Focalized Intraluminal Balloons, filed Oct. 30, 1996, now U.S. Pat. No. 5,843,116, the disclosure of which is incorporated in its entirety herein by reference.

In one particular application, the central zone 32 has an axial length of about 10 mm, and each of the proximal zone 28 and distal zone 30 have an axial length of about 5 mm. At an inflation pressure of about 8 atmospheres, the proximal zone 28 has an outside diameter of about 3 mm, and the central zone 32 has an outside diameter of about 3.4 mm. The same balloon at 18 atmospheres inflation pressure has an outside diameter of about 3.1 mm in the proximal zone 28 and an outside diameter of about 3.5 mm in the central zone 32. That particular balloon was constructed from PET, having a wall thickness of about 0.0006 to about 0.0008 inches.

The overall dimensions of any particular balloon 18 will be governed by the intended use, as will be well understood to those of ordinary skill in the art. For example, balloons can be readily provided having a central zone 32 and inflatable to a diameter of anywhere within the range of from about 1.5 mm to about 10 mm. For coronary vascular applications, the central zone 32 will normally be inflatable to a diameter within the range of from about 1.5 mm to about 4 mm, with balloons available at about every 0.25 mm increment in between.

The proximal zone 28 and distal zone 30 are generally inflatable to a diameter within the range of from about 1.25 mm to about 9.5 mm. For coronary vascular applications, the proximal and distal zones 28, 30 are preferably inflatable to a diameter within the range of from about 1.25 mm to about 3.5 mm.

The axial length of the central section 32 can be varied considerably, depending upon the desired radiation delivery length as will become apparent. For example, the axial length of the central section 32 may be anywhere within the range of from about 0.5 cm to about 5.0 cm or longer. For coronary vascular applications, the axial length of the central section 32 will normally be within the range of from about 0.5 cm to about 2.0 cm, if the balloon is designed to deliver radiation as well as simultaneously perform conventional PTCA. In a radiation delivery balloon which is not intended to perform PTCA, the axial length of the central zone 32 may exceed the typical length of the lesion, and, in coronary vascular applications, the axial length may be within the range of from about 0.5 cm to about 5 cm or longer.

The axial length of the proximal zone 28 and distal zone 30 may also be varied considerably, depending upon the desired performance characteristics. In general, axial lengths of the cylindrical portion of the proximal zone 28 and distal zone 30 at least about 3 mm appear useful.

The stepped balloon 18 can be manufactured using any of a variety of techniques which will be understood to those of skill in the art. For example, the balloon can be manufactured by blowing suitable tubing stock into a stepped mold cavity. Alternatively, the tubing stock can be blown into a first mold having a diameter approximately equivalent to the diameter of the proximal section 28 and distal section 30. The balloon can then be blown into a second mold having a larger diameter section corresponding to the central section 32 in the finished balloon. The balloon is inflated into the larger mold under the application of heat, as will be understood by those of skill in the art.

Variations on the configuration of the balloon 18 can be readily constructed, as desired, depending upon the clinical objective. For example, either the proximal section 28 or the distal section 30 can be eliminated. The proximal section 28 or the distal section 30 can alternatively be provided with a diameter that is greater than the central section 32.

Figure 2:
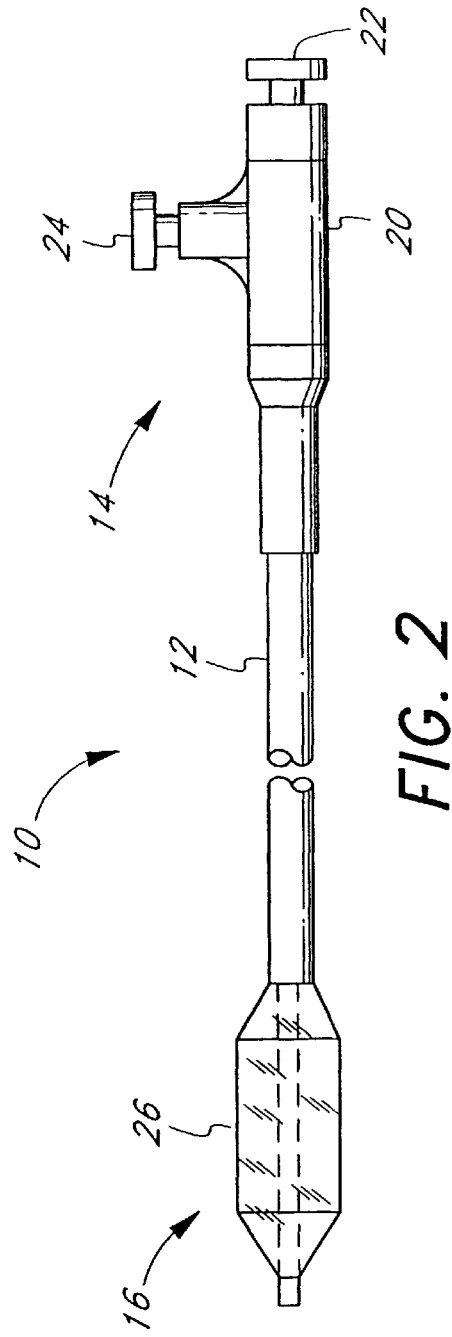
FIG. 2 is a schematic side elevational view of a second embodiment of a balloon catheter in accordance with the present invention.
Figure 2A:
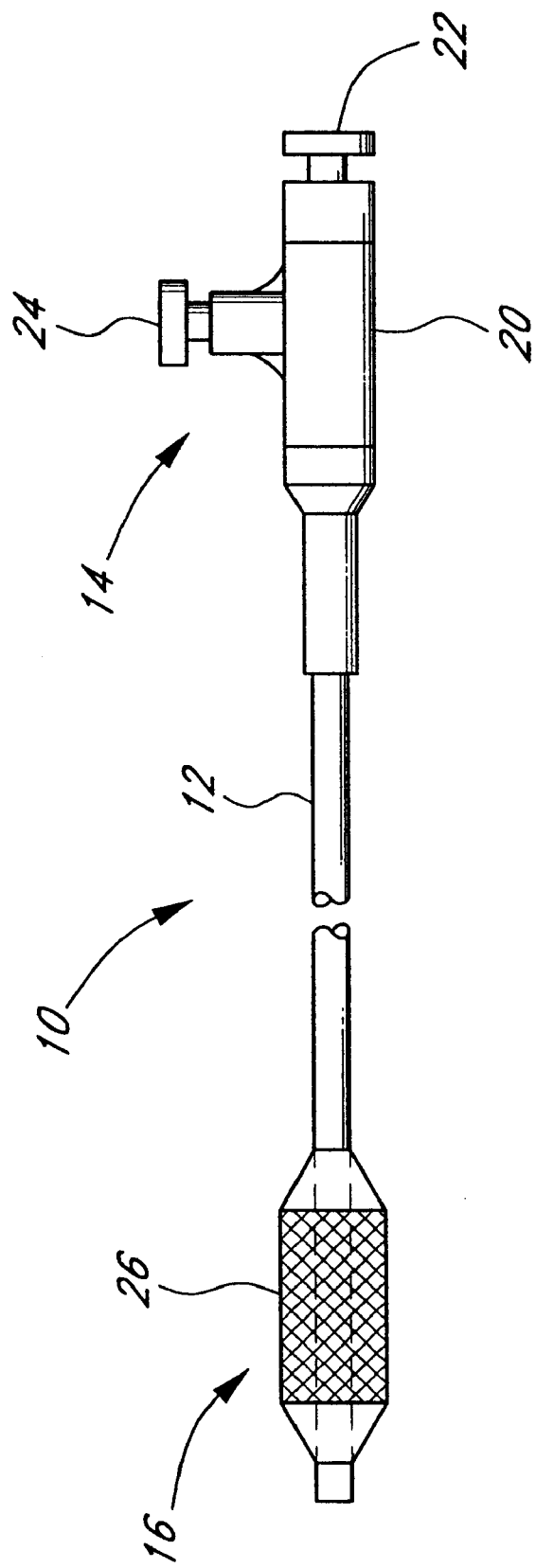
FIG. 2A is a balloon catheter, as illustrated in FIG. 2, having a stent mounted thereon.

In accordance with an alternative embodiment of the balloon of the present invention, illustrated in FIG. 2, the balloon 26 has a generally cylindrical inflated profile throughout its axial working length such as with conventional PTCA balloons. Either the stepped balloon of FIG. 1 or the cylindrical balloon of FIG. 2 can be readily provided with the radiation carrier discussed below in accordance with the present invention.

Figure 4A:
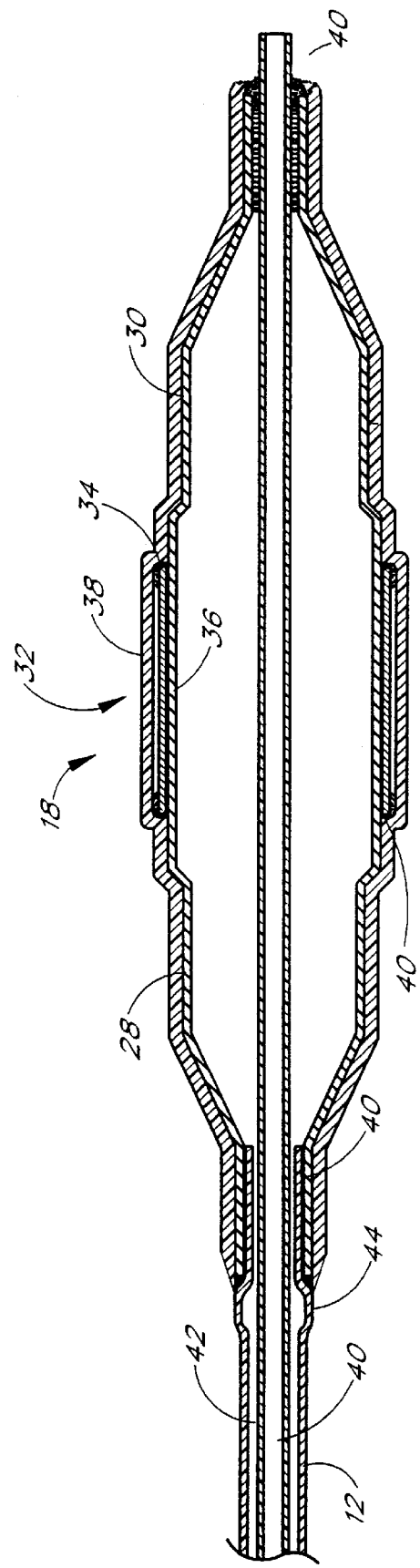
FIG. 4A is a cross-sectional view of a second embodiment of a balloon of the type illustrated in FIG. 3.

Referring to FIGS. 3 and 4, there is disclosed a radioactive balloon in accordance with the present invention, configured as in FIG. 1. In general, the balloon 18 comprises a proximal zone 28, and a distal zone 30 having approximately equivalent inflated diameters. The proximal zone 28 and distal zone 30 are separated by an enlarged central zone 32 as has been discussed. Enlarged zone 32 is provided with a radiation source 34, preferably distributed uniformly throughout the circumference of the balloon.

Referring to FIG. 4, the central zone 32 comprises an inner balloon wall 36 surrounded by the radiation source 34. Preferably, the radiation source 34 is surrounded by an outer sleeve 38. In the illustrated embodiment, the radiation source 34 is entrapped between the outer sleeve 38 and balloon wall 36, and the outer sleeve 38 is adhered to the balloon wall 36 such as through the use of an adhesive 40. Suitable adhesives include medical grade UV curable and urethane adhesives known in the art. Any of a wide variety of techniques known to those of skill in the art can be utilized for securing an outer sleeve 38 to the balloon, such as thermal bonding, heat shrinking, adhesives, spot welding, and the like. In addition, the sleeve 38 as illustrated extends only slightly longer in the axial direction than the axial length of the radiation source 34.

The outer sleeve 38 can alternatively extend the entire length of the balloon, such that it is necked down at the proximal end of the balloon to the catheter shaft and similarly necked down at the distal end of the balloon to the catheter shaft. Preferably, however, to minimize the amount of material contained in the balloon and minimize the insertion profile of the balloon, the outer sleeve 38 extends only as far axially as necessary to secure the radiation source 34. In an alternate embodiment, the outer sleeve 38 extends from a distal point of attachment to the balloon wall as illustrated in the proximal direction all the way to the catheter shaft, since insertion profile on the proximal side of the central zone 32 is less critical than on the distal side thereof. One suitable outer sleeve 38 comprises 0.0003 inch wall thickness PET tube.

Alternatively, the outer sleeve 38 can be omitted, so long as the radiation source 34 is adequately secured to the balloon.

The balloon 18 is mounted on a tubular body 12, which preferably comprises a central guidewire lumen 40 and an inflation lumen 42. In the illustrated embodiment, the two lumen 40 and 42 are illustrated in a concentric relationship as is known in the art. Alternatively, the two lumen 40 and 42 can be formed in a side-by-side geometry, such as through the use of conventional extrusion techniques.

The tubular body 12 is further illustrated as having an optional radial enlargement 44, to facilitate in smoothing the transition between the diameter of the tubular body 12 and the adjacent diameter of the proximal end of the balloon as illustrated. The proximal end of the balloon may be secured to the tubular body 12 and the distal end of the balloon may be secured to the wall defining the guidewire lumen 40 through the use of any of a variety of techniques such as adhesives, as illustrated, heat shrinking, and the like.

The radiation source 34 can comprise any of a variety of materials capable of retaining a radiation charge for a sufficient length of time to deliver a predetermined therapeutic amount of radiation to the treatment site. In general, certain metals appear to be the most efficient radiation source, taking into account the amount of radiation to be retained therein, and the desire to minimize outside diameter of the deflated catheter. Materials such as platinum, phosphorous-32, Yttrium-90, Gold-198 and Iridium-192, among others, may be useful, as well as other metals and non metals having a suitable density depending upon the desired radioactivity and desired deflated balloon profile.

In an alternate embodiment of the invention, the balloon material carries the radioactive charge, so that no separate carrier layer is necessary. This could be accomplished by doping the balloon material with an element or other species that can be neutron activated. For example, a PE or PET multilayer or single layer balloon can be extruded with sodium phosphate (monobasic, dibasic or tribasic) as a filler. The phosphate filled balloon can be placed in a neutron bean to produce sodium phosphate P-32.

Preferably, the filler is uniformly distributed throughout the circumference of the balloon. Sodium phosphate filler will generally be introduced within the range of from about 0.5% to about 10% by weight, although the optimal weight percent will be determined by compromising various variables such as desired radioactivity, crossing profile, flexibility, and others which will be apparent to those of skill in the art in view of the particular filler.

In one embodiment, the radiation source 34 comprises a metal foil such as gold. The metal foil is preferably evenly circumferentially distributed around the balloon 18, and, most preferably, comprises a continuous or substantially continuous annular sleeve. For example, in an embodiment of the catheter intended to have a 10 mm axial length radiation delivery zone, a rectangular strip of metal foil having a width of 10 mm can be rolled around the balloon through one complete revolution, or two or more revolutions to provide multiple layers, depending upon the thickness of the metal foil and desired radiation charge capabilities. Alternatively, the radiation source may comprise a plurality of annular bands or other configurations as will be apparent from the disclosure herein.

Preferably, the radiation source will be evenly circumferentially spaced or distributed around the periphery of the balloon, to provide a substantially continuous and even radiation dose around the wall of the vessel at the treatment site. Alternatively, the radiation source can be positioned to extend only part way around the balloon, such as to treat an asymmetric lesion.

The desired radiation charge will depend in part upon the manner in which the catheter is intended to be handled prior to use at the clinical site. For example, in one embodiment of the invention, the balloon is intended to retain a radioactive charge for an extended period such as two to six months or longer, so that it can be dosed at the point of manufacture and hold the radioactive charge for a reasonable shelf life. Alternatively, considerably shorter dosage retention times are desired if the catheter is designed to be charged at the clinical site, such as within minutes or hours preceding the procedure in which the treatment site within the patient is exposed to the radiation source.

When the catheter is charged at the clinical site, the radiation source 34 may be produced by exposing the carrier (e.g., metal foil) designed to carry the radioactive charge to a stream of neutrons. This technique is known as neutron activation and is one method that is commonly used for transmuting stable (nonradioactive) elements into radioactive ones (An. N. Nesmyanov, *Radiochemistry*, Translated by Artvaz Beknazarov, Mir Publishers, Moscow, 1974). The method is relatively simple, as it involves placing the material to be activated into a flux of neutrons having the required energy. Typically, such a reaction might involve a neutron entering the nucleus of the target atom and a gamma photon exiting it. This is designated as an $(n,\gamma)$ reaction, and it raises the atomic mass of the original isotope by one atomic mass unit. With such a reaction, a new isotope is made of the same element used as the target material. The amount of activity of the new isotope produced is a function of many variables, including the neutron flux and energy used, the nuclear cross section of the desired reaction, the mass and isotopic abundance of the target material, and the half-life of the new isotope that is produced. This last parameter is significant. If the half-life of the new isotope is very long (e.g., $10^9$ years), then very little activity can be produced. Should the new isotope be stable, then no activity will be produced.

An example of radionuclide production by this method is the transmutation of molybdenum-98 to molybdenum-99 by neutron bombardment [$^{98}$Mo $(n,\gamma)^{99}$Mo]. This can be written as $^{98}$Mo+n→$^{99}$Mo+$\gamma$. The threshold reaction energy for this reaction can be calculated by determining the total reaction energy (known as the Q value), and multiplying this by the ratio of the masses of the neutron to the target nucleus (Bernard G. Harvey, *Introduction to Nuclear Physics and Chemistry*, Prentice-Hall, Inc., Englewood Cliffs, N.J., 1969, and Kenneth S. Krane, *Modern Physics*, John Wiley & Sons, New York, 1983). To find the Q value, one sums the mass of the Mo-98 nucleus and neutron, and then subtracts the mass of the resultant Mo-99 nucleus. The resulting difference in mass is converted into energy. Using the masses given by Krane, one obtains: [97.905405 u+1.00866501 u−98.907709 u]931.5 MeV/u=5.92 MeV (Mega electron Volts), where u=atomic mass unit (Dalton). This value is actually slightly high, since the energy of the gamma photon has been neglected. The threshold for the desired reaction is thus $$5.92 \frac{1.00866501u}{97.905405u} = 0.061 \text{ MeV}.$$

Since the calculated Q value is slightly high, this threshold energy for the reaction is also slightly high. Neutrons with energies below one MeV are considered "thermal" (see Nesmyanov reference), i.e., this reaction would proceed with very slow neutrons which are abundant in nuclear reactors.

The actual production rate R of the isotope produced by neutron bombardment (e.g., Mo-99) is governed by the equation:

$$R = \phi \sigma M_t \frac{ap}{MW} N_0$$

in which the production rate is in reactions per second, the neutron flux $\Phi$ is in neutrons per square centimeter per second, the nuclear cross section $\sigma$ is in barns (1 barn=$10^{-24}$ cm$^2$), and the mass of the target is designated as $M_t$. The number of atoms of interest per molecule of target material (given by its chemical formula) is a, and p is the abundance of the isotope of interest. The atomic weight of the target atom is designated as MW, and $N_0$ is Avogadro's number (6.023×10$^{23}$) (*CRC Handbook of Radiation Protection and Measurement* Volume I, Allen Brodsky, Editor, CRC Press, Inc. Boca Raton, Fla., 1985). The production rate can be increased by increasing the flux $\Phi$, target mass $M_t$, or the percent of abundance of the isotope of interest in the target material. Concerning the production of Mo-99 from Mo-98, Mo-98 is only 24.1% abundant in nature. Using enriched molybdenum that is >90% in the 98 mass will greatly increase the production rate.

The activity of the material that is produced is a function of the new isotope's half-life and irradiation time. The activity A, produced is determined by the formula A=R(1−$e^{\lambda t}$) in which e is the base of the Naperian or natural logarithm (i.e., 2.718 . . . ), and the elapsed time is t. $\lambda$ designates the decay constant of the isotope that is formed, and is calculated as the Naperian logarithm of two divided by the half life of the isotope. (It is important that time is measured in the same units in all of these calculations.) It should be noted that after a given time, a saturation point is reached, and no further activity is produced by neutron bombardment, i.e., the material is decaying away as fast as it is being produced. This represents an upper limit for the specific activity of a given isotope that can be produced under these conditions.

The above procedure is useful for producing radioactive isotopes of the same element that is used as the target material (e.g., producing Au-198 from Au-197). Sometimes a different element can be produced by bombarding the target atom with -neutrons. Bombarding aluminum with thermal neutrons will yield Al-28[$^{27}$Al+n→$^{28}$Al+γ]. However, if neutrons with an average energy of 8.1 MeV are used (neutrons with an energy $\geq$1 MeV are termed "fast"), the following reaction occurs: $^{27}$Al+n→$^{24}$Na+α. Another useful reaction using fast neutrons is the bombardment of sulfur (natural sulfur is 95.02% isotope of mass 32): $^{32}$S+n→$^{32}$P+p. The threshold energy of this reaction can be calculated (as in the Mo case), with the following results: [31.972072 u+1.00866501 u−31.973908 u−1.00727647 u]931.5 MeV/u=33.12 MeV. (Once again the masses are from Krane.) The threshold for the desired reaction is:

$$33.12 \frac{1.00866501u}{31.972072u} = 1.04 \text{ MeV}.$$

Experimental observation and measurement show that this is indeed the threshold energy for this reaction, and it reaches its maximum yield at neutron energies of about 2.9 MeV (CRC).

In one embodiment, the radiation source 34 comprises a gold foil, having an axial length as mounted on the balloon of about 1.0 cm, a width sufficient to be rolled up into a cylinder having a diameter of about 3 mm. The thickness of the gold foil is about 0.0003 inches. These dimensions provide a volume of 7.18 E−4 cm. The density of gold, according to the Merck Index, is 19.3 gm/cm$^3$. Such a density gives a mass of 13.9 mg of gold, or 4.23 E+19 atoms of gold to activate.

Gold has a nuclear cross-section of 98.8 barns. The half-life of gold-198 is 2.696 days. Using a reactor having a thermal flux of 2 E+12 neutrons/square cm/second, the following relationship between irradiation time and resultant activity should be observed:

TABLE 1

| Irradiation Time | Resultant Activity |
| --- | --- |
| 0.25 hours | 0.605 mCi |
| 0.50 hours | 1.21 mCi |
| 1.0 hour | 2.41 mCi |
| 2.0 hours | 4.79 mCi |
| 3.0 hours | 7.15 mCi |
| 5.0 hours | 11.8 mCi |
| 8.0 hours | 18.6 mCi |

The amount of radiation delivered using the catheter of the present invention can be varied considerably, depending upon the desired clinical result. In general, many applications of the present invention for use following conventional PTCA will deliver in the range of from about 10 to about 40 Grays over approximately a two minute exposure. More preferably, the catheter will deliver from about 10 to about 20 Grays over approximately a two minute period. For this purpose, metal foils having a density in excess of about 7 grams per centimeter cubed may be used.

By appropriate source selection, radioactive charging time and in vivo dose delivery time, higher radiation delivery can be obtained. Where doses on the order of from about 25 to about 2500 rads per centimeter length of lumen treated, and preferably from about 100 to about 1000, and most preferably about 250 per centimeter length of lumen treated are desired, delivery is preferably accomplished in less than 30 minutes to minimize the amount of time the patient is subject to the procedure. Preferably, the procedure takes less than about 25 minutes. More preferably less than about 15 minutes, but typically it requires at least about 10 minutes.

To deliver this amount of radiation in this time, it may be necessary for the total radiation provided by the radiation source to be from about 100 to about 10,000, preferably from about 500 to about 5,000, and typically about 3000 Rads per hour along the length of the radioactive source 34. This result can be effected if the radioactive source 34 provides from 0.01 to about 100,000 millicuries, and preferably from about 50 to 500, and typically about 100 millicuries per centimeter length of radioactive source 34.

The resultant activity as a function of irradiation time illustrated in Table 1 can be varied considerably by selecting a different thermal flux than 2 E+12 neutrons/cm$^2$/second.

For example, higher resultant activities for the stated irradiation times can be achieved by selecting higher E values. A thermal flux of 6 E, 8 E, 10 E, 12 E, or higher can be used depending upon the material of the radiation carrier, the thickness of the radiation carrier layer, the indwelling time within the patient, and the desired clinical result. Optimizing the radiation dose parameters can be readily accomplished through routine experimentation by one of skill in the art in view of the disclosure herein, depending upon the desired clinical method.

Although the parameters will most likely be optimized through clinical procedures, the radiation dose required can be roughly estimated from physical considerations. It is helpful to first consider the case of a radiation point source, such as phosphorous-32 (P-32), several of whose key radiation parameters are listed here:

Half-life=14.28 days

Maximum Beta Energy=1.71 MeV

Average Beta Energy=0.6948 MeV

Betas Per Nuclear Disintegration=1.00

Maximum Range in Tissue=0.80 cm

Where the maximum range in tissue is related to the maximum beta energy.

Figure 5:
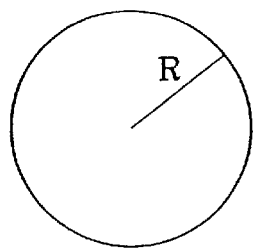
FIGS. 5, 6a and 6b show geometrical relationships which are relevant to radiation dose calculations.

The following calculations give the activity that yield a dose of 12 Grays in 5 hours to the tissue surrounding the radiation point source. It is assumed that the radionuclide will bombard the tissue continuously for five hours and then be removed. When the implanted P-32 is a point source, the distribution of beta particles will be in a spherical pattern emanating from the center of a sphere with a radius of 0.80 cm, as illustrated in FIG. 5. Since the volume of a sphere is $4/3\pi r^3$, the corresponding spherical volume of tissue is 2.17 cm$^3$. Assuming a density ($\rho$) of the tissue essentially equal to that of water, this gives a mass of 2.17 grams. If a total absorbed dose of 12 Grays is required over a period of 5 hours, the initial dose rate will decrease only slightly with the 14.28 day (342.72 hour) half life of P-32. This gives a decay constant ($\lambda$) of 0.002002/hour [ln2/342.72 hours]. The accumulated dose in 5 hours can be determined exactly by the integral 12 Grays=

$$\int_0^5 Re^{-0.002002t} dt,$$

where R is the initial dose rate in Rads per hour, and t is the elapsed time. Evaluating this integral gives a value for R of approximately 2.4 Grays per hour. It should be noted that the 14 day half-life is sufficiently long relative to the 5 hour irradiation time that the decay of the P-32 could have been ignored.

The initial activity required to deliver the desired dose can be determined by beginning with the definition of a Gray, namely, one Joule of energy absorbed per kilogram of material. Since 2.4 Grays/hour are absorbed by 2.17 grams of tissue, this amounts to $$2.4 \frac{J/kg}{hour} \times 0.00217 \text{ kg} = 0.00520$$

J/hour of absorbed energy by the tissue, which is equal to $$3.25 \times 10^{10} \frac{MeV}{hour}.$$

Since 0.6948 MeV of energy are released per disintegration, this gives a required P-32 activity of $4.67 \times 10^{10}$ disintegrations per hour, or $1.30 \times 10^7$ Bq, or 351 $\mu$Ci.

As an alternative to P-32, other radionuclides such as Yttrium-90 (Half-life=64.0 hours; Maximum Beta Energy= 2.27 Mev; Average Beta Energy=0.9314 MeV; Betas Per Nuclear Disintegration=1.00; Maximum Range in Tissue= 1.11 cm); Gold-198 (Half-life=2.696 Days; Maximum Beta Energy=961 keV; Average Beta Energy=316.3 keV; Betas Per Nuclear Disintegration=1.00; Maximum Range in Tissue=0.42 cm); and Iridium-192 (Half-life=74.2 Days; Maximum Beta Energy=666 kev; Average Beta Energy=222 keV; Maximum Range in Tissue=0.25 cm) may also be useful.

Figure 6A:
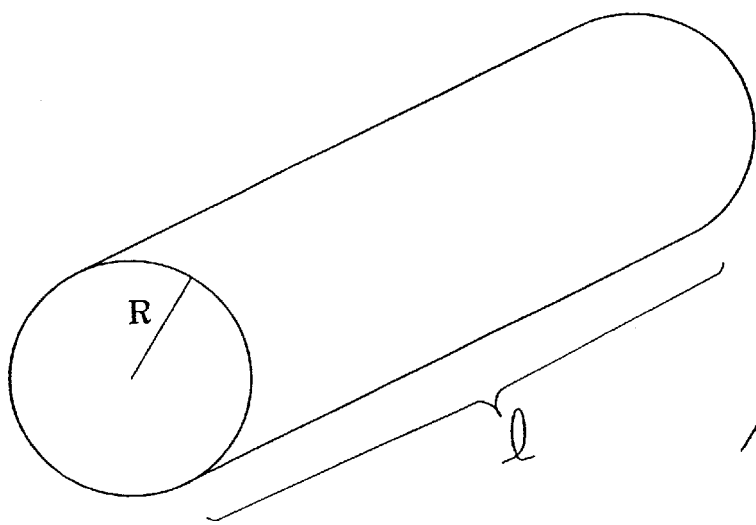
Figure 6B:
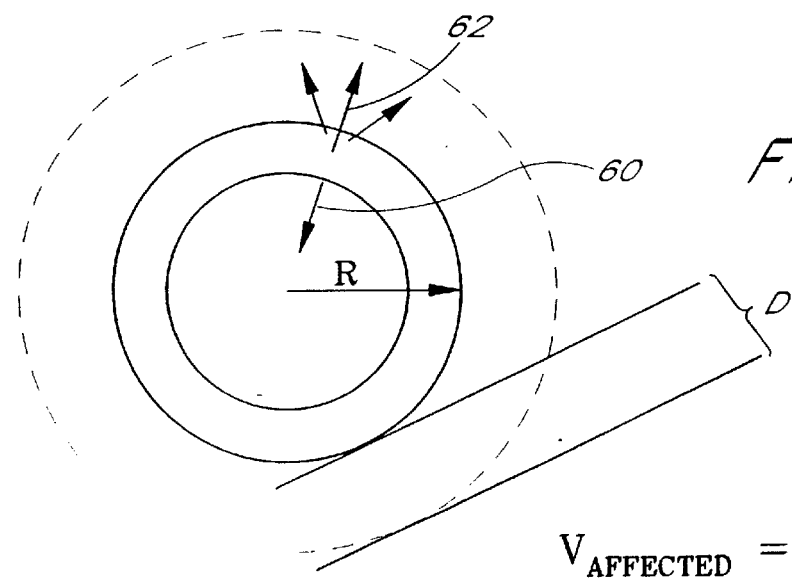

There are differences in geometry between the radiation delivery balloon of the present invention and a point source which lead to significant differences in how radiation is distributed in the tissue, as illustrated in FIGS. 6a and b. Whereas a point source results in a spherical distribution of radiation, the catheter produces a distribution of radiation that has cylindrical symmetry. Assuming a radiation penetration depth of D and a catheter of length l and radius r, the volume of tissue affected by a catheter wrapped in a radiation source can be roughly estimated as $$Vol_{cath} = l\pi(r+D)^2 - l\pi r^2$$

This quantity depends explicitly on the catheter's length l and radius r.

Actually, radiation leaving either a point source or a cylindrical one has a distribution of beta decay energies, and there is a nonuniform distribution of energy deposited within the absorbed tissue: it is easier to expose tissue closer to the radiation source to 12 Grays, as tissue further away from the radiation source is partially blocked. This means that in order to expose all of the desired tissue to a desired dose such as 12 Grays, tissue closer to the radiation source will be exposed to more than 12 Grays, and more radiation is required than a simple model of uniform distribution would suggest. Furthermore, some of the radiation may pass through the tubular body 12 before reaching tissue (i.e. radiation whose direction of propagation is given by arrows 60 as opposed to 62) depending upon the stopping power of the inflation media and materials that make up the catheter. In any case, those skilled in the art will appreciate that the optimal radiation dose and related parameters will be determined by routine experimentation and clinical study.

In an embodiment using PET or other substantially noncompliant material, it is unnecessary that the gold foil or other radiation delivery media be able to elastically expand with inflation of the balloon. Instead, the balloon can be assembled in the inflated configuration, and then deflated so that the gold foil is folded with the PET balloon into the insertion profile.

In accordance with the method of the present invention, a balloon catheter such as any described above is manufactured and shipped without a radioactive charge. At the clinical site, the catheter is placed in a reactor and charged for a sufficient period of time to dose the balloon. The balloon is thereafter percutaneously inserted and transluminally advanced through a patient's vasculature, to the treatment site. At the treatment site, the balloon is expanded to position the radioactive delivery layer against the vessel wall. The balloon remains expanded for a sufficient radiation delivery time, and is thereafter deflated and withdrawn from the patient. The balloon may be introduced through an introduction sheath, which can be proximally withdrawn to expose the balloon once the balloon has been positioned at the treatment site. However, due to the relatively low penetration of, for example, gold 198 radiation, a protective sheath is generally unnecessary.

If delivery times greatly in excess of one or two minutes are clinically desirable, the catheter 10 may be provided with a perfusion conduit. In general, perfusion capabilities can be added to the radiation delivery balloon of the present invention by providing an axially extending perfusion lumen through the balloon (not illustrated). One or more perfusion apertures is provided on the catheter shaft on the proximal side of the balloon, for permitting communication between the perfusion conduit and the outside of the catheter, and one or more perfusion apertures is provided on the distal side of the balloon for permitting blood to bypass the balloon as will be understood by those of skill in the art. Any of a variety of perfusion structures can be utilized, such as any of those disclosed in U.S. Pat. No. 5,344,402 to Crocker entitled Low Profile Perfusion Catheter or U.S. Pat. No. 5,421,826 to Crocker et al. entitled Drug Delivery and Dilatation Catheter Having a Reinforced Perfusion Lumen, the disclosure of each of which is incorporated in its entirety herein by reference.

In accordance with another aspect of the method of the present invention, a radiation delivery and balloon dilatation catheter 10 is utilized to simultaneously dilate a stenosis in a vessel and deliver a treating dose of radiation. The catheter of either FIG. 1 or 2 is percutaneously introduced and transluminally advanced through the arterial system to reach a stenosis. The balloon is positioned within the stenosis, and inflated to expand the stenosis as is known in the art. During the expansion step, the balloon is delivering a treatment dose of radiation to the vessel wall. The balloon may then be left in position in the inflated profile for a sufficient period of time to deliver the desired dose of radiation. The balloon is thereafter deflated, and the catheter is withdrawn from the treatment site.

Thus, in accordance with the present invention, there is provided a catheter having a radiation delivery layer on the balloon, which permits a relatively low energy radiation delivery source to be positioned directly against, or within about 0.01 inches and preferably no more than about 0.003 inches from the vascular wall, depending upon the thickness of any outer sleeve 38 or other coating. In addition, the present configuration expels substantially all blood or other fluids from between the radiation source and the vessel wall, throughout the entire interior circumference of the vessel for the axial length of the balloon. As a consequence, the radiation is not required to penetrate multiple structures as well as blood within the vessel in order to reach the vessel wall. In addition, radiation delivery is essentially uniform throughout the entire circumference of the vessel at the delivery site.

The configuration of the balloon of the present invention is such that the radiation delivery layer does not need to be elastic and can simply be folded with the balloon material into the reduced, insertion profile. Higher radiation dosages than those specifically described herein can be readily achieved, such as through the use of longer dose times and/or metal films or layers having a physical capability to carry a higher radiation dosage.

Although the present invention has been described in terms of certain preferred embodiments, other embodiments of the invention will become apparent to those of skill in the art in view of the disclosure herein. Accordingly, the scope of the present invention is not intended to be limited by the foregoing, but rather by reference to the attached claims.

What is claimed is:

1. A radiation delivery balloon catheter, comprising:
    an elongate flexible tubular body having a proximal end and a distal end;
    an inflatable balloon on the tubular body having a proximal end, a distal end and a working length therebetween, said balloon in fluid communication with an inflation lumen extending axially through the tubular body;
    a substantially inelastic radiation source secured to the balloon; and
    an outer tubular sleeve surrounding the radiation source, wherein the sleeve is necked down to the tubular body proximally and distally beyond the working length of the balloon.

2. A radiation delivery balloon catheter as in claim 1, wherein the radiation source is no more than about 0.001 inches thick.

3. A radiation delivery balloon catheter as in claim 1, wherein the radiation source is within the range of from about 0.0001 inch to about 0.009 inch thick.

4. A radiation delivery balloon catheter as in claim 1, further comprising a guide wire lumen extending axially throughout at least a portion of the catheter.

5. A radiation delivery balloon catheter as in claim 4, further comprising a proximal guide wire access port on the tubular body, positioned distally of the proximal end of the tubular body.

6. A radiation delivery balloon catheter as in claim 1, further comprising a perfusion conduit extending through the tubular body from a proximal side of the inflatable balloon to a distal side of the inflatable balloon, at least a first perfusion port on the tubular body on the proximal side of the balloon and at least a second perfusion port on the tubular body on the distal side of the balloon.

7. A radiation delivery balloon catheter as in claim 1, further comprising an implantable stent mounted on the balloon.

8. A radiation delivery balloon catheter as in claim 1, wherein the balloon comprises a central section having a larger inflated diameter than a proximal section and a distal section.

9. A radiation delivery balloon catheter as in claim 1, wherein the radiation delivery source comprises a metal.

10. A radiation delivery balloon catheter as in claim 1, wherein the radiation delivery source is selected from the group consisting of Pt, P-32, Y-90, Au-198, Ir-192, Mo-99, and combinations thereof.

11. A radiation delivery balloon catheter as in claim 1, wherein the radiation delivery source is doped into the material of the balloon.

12. A radiation delivery balloon catheter as in claim 1, wherein the radiation delivery source comprises a non metal.

13. A radiation delivery balloon catheter as in claim 1, wherein the radiation delivery source is tubular.

14. A radiation delivery balloon catheter as in claim 1, wherein the radiation delivery source is annular.

15. A radiation delivery balloon catheter as in claim 1, wherein the radiation delivery source has a proximal end, a distal end, and a length therebetween, and the source is continuous along the length.

16. A radiation delivery device, comprising:
    an elongate flexible tubular body having a proximal end and a distal end;

a substantially inelastic radially expandable support member on the tubular body;

a radiation source carried by the support member; and an outer tubular sleeve surrounding the radiation source, wherein the sleeve is necked down to the tubular body proximally and distally of the source, and wherein the support member is expanded by means non-removably attached thereto.

17. A radiation delivery device as in claim 16, wherein the support member is an inflatable balloon.

18. A radiation delivery device as in claim 17, wherein the balloon is provided with a central section having a larger inflated diameter than a proximal section and a distal section.

19. A radiation delivery device as in claim 16, further comprising a guide wire lumen extending axially throughout at least a portion of the device.

20. A radiation delivery device as in claim 19, further comprising a proximal guide wire access port on the tubular body, positioned distally of the proximal end of the tubular body.

21. A radiation delivery device as in claim 16, further comprising a perfusion conduit extending from a proximal side of the support member to a distal side of the support member.

22. A radiation delivery device as in claim 16, wherein the radiation source comprises a beta-emitting isotope.

23. A radiation delivery device as in claim 16, wherein the radiation source is annular.

24. A radiation delivery device as in claim 16, wherein the radiation source is tubular.

25. A radiation delivery device as in claim 16, wherein the radiation delivery source has a proximal end, a distal end, and a length therebetween, and the source is continuous along the length.

26. A radiation delivery device as in claim 16, wherein the radiation source is integral with the support.

27. A radiation delivery device as in claim 16, wherein the radiation source is layered upon the support.

28. A method of treating a site within a vessel, comprising the steps of:

identifying a site in a vessel to be treated;

providing a radiation delivery catheter including an elongate flexible tubular body having radiation source carried by a substantially inelastic radially expandable support and an outer sleeve surrounding the radiation source, wherein the outer sleeve is necked down to the tubular body proximally and distally of the radiation source, and wherein the support member is expanded by means non-removably attached thereto;

positioning the radiation source within the treatment site;

expanding the expandable support to position the radiation source against the vessel wall;

delivering a circumferentially substantially uniform dose of radiation from the radiation source to the vessel wall; and thereafter contracting the expandable support and removing said support from the treatment site.

29. A method as in claim 28, wherein the expanding step comprises inflating an inflatable balloon.

30. A method as in claim 29, wherein the expanding step comprises expanding a central section of the balloon having a larger inflated diameter than a proximal section and a distal section of the balloon.

31. A method as in claim 28, further comprising the step of perfusing blood from a proximal side of the expandable support to a distal side of the expandable support.

32. A method as in claim 28, wherein the catheter further comprises a proximal guide wire access port on the tubular body, positioned distally of the proximal end of the tubular body.

33. A method as in claim 28, wherein the radiation source comprises a beta-emitting isotope.

34. A method as in claim 28, wherein the radiation source is annular.

35. A method as in claim 28, wherein the radiation source is tubular.

36. A method as in claim 28, wherein the radiation source has a proximal end, a distal end, and a length therebetween, and the source is continuous along the length.

37. A method as in claim 28, wherein the positioning step comprises positioning the source within a stent.

38. A method as in claim 28, wherein the radiation source is integral with the support.

39. A method as in claim 28, wherein the radiation source is layered upon the support.

40. A radiation delivery catheter, comprising:

an elongate flexible tubular body having a proximal end and a distal end;

a substantially inelastic radially expandable support on the tubular body, wherein the support is expanded by means non-removably attached thereto;

a radiation source carried by the support; and a cover surrounding the radiation source extending from the body proximally of the source to the body distally of the source.

41. A radiation delivery catheter as in claim 40, wherein the support is an inflatable balloon.

42. A radiation delivery catheter as in claim 41, wherein the balloon is provided with a central section having a larger inflated diameter than a proximal section and a distal section.

43. A radiation delivery catheter as in claim 40, further comprising a guide wire lumen extending axially throughout at least a portion of the catheter.

44. A radiation delivery catheter as in claim 40, further comprising a proximal guide wire access port on the tubular body, positioned distally of the proximal end of the tubular body.

45. A radiation delivery catheter as in claim 40, further comprising a perfusion conduit extending from a proximal side of the support to a distal side of the support.

46. A radiation delivery catheter as in claim 40, wherein the radiation source comprises a beta-emitting isotope.

47. A radiation delivery catheter as in claim 40, wherein the radiation source is annular.

48. A radiation delivery device as in claim 40, wherein the radiation source is tubular.

49. A radiation delivery device as in claim 40, wherein the radiation source has a proximal end, a distal end, and a length therebetween, and the source is continuous along the length.

50. A radiation delivery device as in claim 40, wherein the radiation source is integral with the support.

51. A radiation delivery device as in claim 40, wherein the radiation source is layered upon the support.

52. A method of treating a site within a lumen, comprising the steps of:

identifying a site in a lumen to be treated;

providing a radiation delivery catheter including an elongate flexible tubular body having a radiation source carried by a substantially inelastic radially expandable support and a cover surrounding the radiation source extending from the body proximally of the source to the body distally of the source;

positioning the radiation source within the treatment site;

radially expanding the expandable support using means fixedly attached to the support to position the radiation source against the wall of the lumen;

delivering a circumferentially substantially uniform dose of radiation from the radiation source to the wall; and radially contracting the expandable support and removing the catheter from the treatment site.

53. A method as in claim 52, wherein the expanding step comprises inflating an inflatable balloon.

54. A method as in claim 53, wherein the expanding step comprises expanding a central section of the balloon having a larger inflated diameter than a proximal section and a distal section of the balloon.

55. A method as in claim 52, further comprising the step of perfusing blood from a proximal side of the expandable support a distal side of the expandable support.

56. A method as in claim 52, wherein the catheter further comprises a proximal guide wire access port on the tubular body, positioned distally of the proximal end of the tubular body.

57. A method as in claim 52, wherein the radiation source comprises a beta-emitting isotope.

58. A method as in claim 52, wherein the radiation source is annular.

59. A method as in claim 52, wherein the radiation source is tubular.

60. A method as in claim 52, wherein the radiation source has a proximal end, a distal end, and a length therebetween, and the source is continuous along the length.

61. A method as in claim 52, wherein the radiation source is integral with the support.

62. A method as in claim 52, wherein the radiation source is layered upon the support.

63. A method as in claim 52, wherein the positioning step comprises positioning the radiation source within a stent.

64. A method as in claim 52, wherein the lumen is selected from the group consisting of large and small arteries, large and small veins, hollow organs, surgically created pathways, esophagus, trachea, urethra, ureters, fallopian tubes, intestines and colon.

* * * * *

UNITED STATES PATENT AND TRADEMARK OFFICE
CERTIFICATE OF CORRECTION

PATENT NO.    : 6,699,170 B1
DATED         : March 2, 2004
INVENTOR(S)   : Michael Crocker, George F. Kick and Mark A. Siminuk It is certified that error appears in the above-identified patent and that said Letters Patent is hereby corrected as shown below:

Title page,
Item [54], Title, please delete the word "BALLOON".

Signed and Sealed this

Thirtieth Day of November, 2004

JON W. DUDAS
*Director of the United States Patent and Trademark Office*